(12) United States Patent
Ross et al.

(10) Patent No.: US 7,537,680 B2
(45) Date of Patent: *May 26, 2009

(54) MIXING REACTIONS BY TEMPERATURE GRADIENT FOCUSING

(75) Inventors: David J. Ross, Silver Spring, MD (US); Michael J. Tarlov, Bethesda, MD (US); Karin M. Balss, Basketing Ridge, NJ (US)

(73) Assignee: The United States of America as represented by the Secretary of Commerce the National Institute of Standards & Technology, Washington, DC (US)

( * ) Notice: Subject to any disclaimer, the term of this patent is extended or adjusted under 35 U.S.C. 154(b) by 865 days.

This patent is subject to a terminal disclaimer.

(21) Appl. No.: 11/039,904

(22) Filed: Jan. 24, 2005

(65) Prior Publication Data

US 2005/0145495 A1  Jul. 7, 2005

Related U.S. Application Data

(63) Continuation-in-part of application No. 10/197,331, filed on Jul. 18, 2002, now Pat. No. 7,029,561.

(60) Provisional application No. 60/588,237, filed on Jul. 15, 2004, provisional application No. 60/323,404, filed on Sep. 19, 2001, provisional application No. 60/307,691, filed on Jul. 25, 2001.

(51) Int. Cl.
   *G01N 27/447* (2006.01)

(52) U.S. Cl. .................................... 204/450; 204/452
(58) Field of Classification Search ......... 204/600–605, 204/450–455
See application file for complete search history.

(56) References Cited

U.S. PATENT DOCUMENTS 5,810,985 A * 9/1998 Bao et al. .................... 204/451
7,029,561 B2 * 4/2006 Ross et al. ................... 204/451

OTHER PUBLICATIONS

Zhu, Spatial temperature gradient capillary electrophoresis for DNA mutation detection, Electrophoresis 2001, 22, 3683-3687.*

* cited by examiner

*Primary Examiner*—Alex Noguerola
(74) *Attorney, Agent, or Firm*—Stites & Harbison PLLC; Ross F. Hunt, Jr.; Stephen J. Weyer

(57) ABSTRACT

A method is provided for observing mixing interactions and reactions of two materials in a fluid. The method in one form provides for concentrating by balancing electrophoretic velocities of a material against the bulk flow of fluid in the presence of a temperature gradient. Using an appropriate fluid, the temperature gradient can generate a corresponding gradient in the electrophoretic velocity of the material so that the electrophoretic and bulk velocities sum to zero at a unique position and the material will be focused at that position. A second material can then be introduced into the fluid and allowed to move through and interact with the focused band of the first material. Products of the interaction can then be detected as they are focused at a different position along the gradient. The method can be adapted to study the temperature dependence of the molecular interaction.

29 Claims, 9 Drawing Sheets

PRIOR ART

MIXING REACTIONS BY TEMPERATURE GRADIENT FOCUSING

CROSS-REFERENCE TO RELATED APPLICATIONS

This application is a continuation-in-part of U.S. patent application Ser. No. 10/197,331 filed on Jul. 18, 2002 now U.S. Pat. No. 7,029,561 B2; which claims benefit of the filing date of both Provisional Patent Application Nos. 60/307,691, filed on Jul. 25, 2001, and 60/323,404, filed on Sep. 19, 2001 and this application claims benefit of the filing date of Provisional Patent Application No. 60/588,237 filed on Jul. 15, 2004.

STATEMENT REGARDING FEDERALLY SPONSORED RESEARCH

This invention was made by employees of the United States Government and may be manufactured and used by or for the Government for governmental purposes without the payment of any royalties.

FIELD OF THE INVENTION

The present invention relates to a method for electrokinetic focusing of materials in a fluid, and in particular, methods for electro-focusing materials in fluidic devices using electric field gradients.

BACKGROUND OF THE INVENTION

Over the past decade a great deal of research has been focused on the development of technology related to micro-total-analytical systems. This technology is based on the concept of a series of microfluidic channels also known as microchannels for the movement, separation, reaction, and/or detection of various materials such as chemicals; biological compounds such as amino acids, proteins, and DNA; or cells or colloidal particles.

One disadvantage with prior microfluidic devices and methods is that there is frequently a mismatch between the extremely small quantities of sample material used for analysis and the often much larger quantities needed for loading the sample into the microfluidic device and transporting the sample to the point of analysis. For example, a typical analysis sample may be around one nanoliter or less of a liquid containing one or materials that is injected into a separation channel and then separated electrokinetically as it moves down the channel to a detection region. However, the channels used to transport the sample materials to the injection point are typically also filled with the sample, thus increasing the required amount of the sample by a factor of 100 or more. In addition, the sample is typically loaded onto the microfluidic device into a reservoir from a pipette so that in all, approximately 99.9% of the sample is discarded as waste.

One general way of addressing the problem of requiring a large sample for analysis is to use any one of a number of focusing techniques. In the context of this disclosure, "focusing" refers to methods for manipulating the velocity of a material and thereby causing it to move towards a position at which the velocity is zero. At the zero velocity position the material will accumulate and increase in concentration, i.e., it will become focused. In addition, the location of the zero velocity position is often dependent upon some characteristic of the material or molecule being focused, so that different materials are focused at different positions, and can thereby be separated.

In this context, focusing is to be distinguished from stacking, which is a related class of methods. Stacking involves moving materials through a velocity gradient (which is often transient) so that the materials accumulate along the velocity gradient. However with stacking, there is no point where the material velocity is zero. Hence, in stacking methods the maximum degree to which material concentration can be increased is theoretically limited to the ratio of the velocities on the fast and slow sides of the velocity gradient. In contrast, for focusing at a zero velocity position, there is no theoretical limit to the concentration factor.

Prior focusing methods include isoelectric focusing; electromobility focusing; counteracting chromatographic electrophoresis; temperature gradient focusing, disclosed in U.S. Patent Application Publication No. 2003/0019752, herein incorporated by reference; and most recently, chiral temperature gradient focusing, disclosed in co-pending U.S. patent application Ser. No. 11/039,955, herein incorporated by reference; and micellar affinity gradient focusing, disclosed in U.S. Patent Application Publication No. 2004/0206626, herein incorporated by reference. With the exception of the recently described micellar affinity gradient focusing method, the focusing methods all separate different materials based upon their electrophoretic properties, e.g., mobility in the case of electromobility focusing and temperature gradient focusing, and the isoelectric point in the case of isoelectric focusing.

Electric field gradient or electromobility focusing is one technique which can be used to concentrate samples at a given position within a microfluidic device before the analysis step. Further, the electric field gradient can be used to concentrate the entire sample at the beginning of the separation channel so that very little of the sample would be wasted.

Electric field gradient focusing is accomplished by the application of an electric field gradient within a microchannel. In response to the electric field gradient, there is a corresponding gradient in the electrophoretic velocity of any ionic material within the microchannel. The total velocity of the material is the sum of its electrophoretic velocity and the bulk fluid velocity. If these two components of the velocity are in opposite directions, they can be balanced so that the material will have zero total velocity.

When there is a gradient in the electrophoretic velocity, the balance between bulk and electrokinetic velocities can occur at a single position along the microchannel and therefore can result in focusing of the material at that position. Typically, the electric field gradient used in focusing is generated by the external manipulation of the electric field in the middle of the microchannel through the use of conducting wires, salt bridges, porous membranes, or other structures that will pass electric current but will restrict the flow of bulk fluid and the materials that are to be focused.

Several recent developments with regard to focusing methods in microfluidics, and in particular, the use of electric field gradients, have been made. A description of related methods of focusing can be found in C. F. Ivory, W. S. Koegler, R. L. Greenlee, and V. Surdigio, Abstracts of Papers of the American Chemical Society 207, 177-BTEC (1994); C. F. Ivory, Separation Science and Technology 35, 1777 (2000); Z. Huang and C. F. Ivory, Analytical Chemistry 71, 1628 (1999); W. S. Koegler and C. F. Ivory, Journal of Chromatography a 726, 229 (1996); and P. H. Ofarrell, Science 227, 1586 (1985), all of which are hereby incorporated by reference.

To illustrate the basic principles disclosed in these publications, reference is made to FIG. 1(a) which depicts a length of fluid-filled microchannel of constant cross-sectional area with an electrode, denoted 4, in the middle, and two further electrodes at each end, denoted 3 and 5, so that the voltages $V_1$, $V_3$ at the ends and the voltage $V_2$ at the middle of the channel can be controlled. A single negatively charged material to be focused is present in a fluid that is provided to the microchannel. The electrical connection, represented as electrode 4, can be accomplished with a simple metal wire as depicted in FIG. 1(a), or through a more complicated structure consisting of additional fluid channels and porous membrane structures or salt bridges.

The electric field in the section 1, i.e., the channel between electrodes 3 and 4 is $E_1=(V_2-V_1)/(l/2)$ and the electric field in section 2, i.e., between electrodes 4 and 5, is $E_2=(V_3-V_2)/(l/2)$, where $V_1$, $V_2$, and $V_3$ are the voltages applied to the three electrodes 3, 4, and 5, and l is the length of the microchannel. If $E_1$ differs from $E_2$ as shown in FIG. 1(b), the electrophoretic velocity of the material in the channel, $u_{EP}$, will be different in section 1 than in section 2. If an overall bulk fluid velocity, $u_B<0$, is applied, e.g., either electro-osmotic or pressure-driven, the bulk fluid velocity must be the same, due to continuity, in all parts of the microchannel. The total velocity of the material, $u_T=u_B+u_{EP}$, will then be the sum of the electrophoretic and bulk velocities, which can differ in section 1 from section 2.

The use of the microchannel device of FIG. 1(a) for focusing of the material is illustrated in FIG. 2 where $u_{T,1}>0>u_{T,2}$, so that the material moves into the middle from both directions and is thus focused in the middle of the channel near electrode 4.

One major drawback to electric field gradient focusing is that the microchannel device tends to be difficult to construct and that it requires the control of voltage on an additional electrode, e.g. 4 of FIG. 1(a), which is used to apply the electric field gradient. In addition, if electrodes are used to generate electric field gradients, unwanted chemical products will be generated electrochemically at the fluid-electrode interface. If the electric field gradient is produced through the use of a salt bridge or membrane, the electrochemical products can be avoided, however only materials that cannot pass through the membrane or salt bridge can be focused.

Two additional methods for concentrating a sample include sample stacking and field amplified sample injection in which a sample is concentrated as the sample crosses a boundary between low and high conductivity fluids. These methods can achieve preconcentration factors of 100 to 1000-fold although these methods require multiple fluids. Sweeping is yet another concentration method which is capable of a very high degree of sample concentration (e.g., up to 5000-fold), but is useful only for small hydrophoic molecules with a high affinity for a mobile micellar phase.

An additional technique for concentrating an ionic material includes isoelectric focusing. Isoelectric focusing is commonly used for the concentration and separation of proteins and involves the focusing of materials at their respective isoelectric points along a pH gradient.

Two examples of recent isoelectric focusing techniques are provided by U.S. Pat. No. 3,664,939 to Luner et al. and U.S. Pat. No. 5,759,370 to Pawliszyn. Both references relate to isoelectric focusing with pH gradients that are created by the application of a temperature gradient. Isoelectric focusing uses a pH gradient to focus materials and in particular proteins, at positions along the pH gradient where the local pH is equal to the isoelectric points of the materials. The isoelectric point is the pH at which the material has zero electrophoretic mobility, i.e., approximately zero charge. pH gradients for isoelectric focusing are typically generated using ampholyte mixtures or immobilized ampholytes in gels. The two above referenced patents are included here as examples of prior art uses of temperature gradients for focusing. It is, however, very unusual for isoelectric focusing to be done with a pH gradient generated using a temperature gradient.

One disadvantage of isoelectric focusing is that it is limited in application because it can only be used with materials having an accessible isoelectric point such as proteins and peptides. Additionally, the concentration to which a protein can be focused with isoelectric focusing is severely limited due to the low solubility of most proteins at their isoelectric points.

BRIEF SUMMARY OF THE INVENTION

Broadly speaking, the present invention involves temperature gradient focusing, in conjunction with the concept that a molecular species or other material in a fluid can be focused and thereby spatially localized, e.g., as a focused band, and then allowed to interact or mix with another molecular species or material that is carried by a bulk fluid flow or electrophoresis through the focused band of the first material. If the interaction, binding, or reaction of the two materials produces a third material, that third material can then also be focused on the temperature gradient. Detection of the focused band of the third material, which is the product of the interaction or reaction of the first two materials, signals that the interaction has occurred. If the product of the interaction is a duplex of the first two materials, further manipulations can then be used to determine the strength of the binding of that duplex by measuring its melting curve and melting temperature.

In the context of this disclosure, "duplex" refers to a pair of two different molecular species or other subject materials that are bound together through specific or non-specific interactions, including biochemical, physiological, and/or pharmaceutical interactions. Examples of types of molecules or materials that would typically be involved in duplex formation include: proteins, nucleic acids, glycoproteins, carbohydrates, hormones, pharmaceuticals, antibodies, and aptamers. Specific examples of duplex forming pairs include: DNA/DNA, DNA/PNA, DNA/RNA, RNA/PNA, antibody/antigen, antibody/hapten, nucleic acid aptamer/protein, drug molecule/drug target molecule, enzyme/substrate, enzyme/inhibitor, enzyme/cofactor, binding protein/substrate, carrier protein/substrate, lectin/carbohydrate, receptor/hormone, receptor/effector, ligand/cell surface receptor, virus/ligand, etc.

Temperature gradient focusing is conducted using a method and device for concentrating and separating materials in a fluid within fluid conduits which include channels, microchannels, and capillary tubes. The concentration is achieved by balancing the electrophoretic velocity of a material against the bulk flow of fluid in the presence of a temperature gradient. Using an appropriate fluid, the temperature gradient can generate a corresponding gradient in the electrophoretic velocity of the material so that the electrophoretic and bulk velocities sum to zero at a given position and the material will be focused at that position.

One aspect of the present invention concerns a method for analyzing the interaction between a first material and a second material in a fluid. The interaction gives rise to a third material. The method includes the steps of introducing a first material into a fluid and applying an electric field to the fluid thereby causing the first material to move electrophoretically with an electrophoretic velocity. A temperature grading is established in the fluid having a significant component substantially aligned with the electrophoretic motion of the first material, thereby generating a gradient in the electrophoretic velocity of the first material. A flow is produced in the fluid having a significant component substantially aligned with a direction opposite a direction of the electrophoretic motion of the first material. The magnitudes of the electric field, temperature gradient and the flow are such that the first material will accumulate or be focused at a first position along the temperature gradient. A second material is introduced to the fluid so that the second material moves through the first position, thereby interacting with the first material to form a third material. The third material of the interaction is focused at a position along the temperature gradient.

In accordance with another aspect of the present invention, a method is provided for determining the melting temperature of a duplex of a first molecular species and a second molecular species in a fluid. The method includes mixing a first molecular species and a second molecular species in a fluid to form a sample solution containing a duplex. An electric field is applied to the fluid thereby causing the duplex to move electrophoretically with an electrophoretic velocity. A temperature gradient is established in the fluid having a significant component substantially aligned with the electrophoretic motion of the duplex, thereby generating a gradient of the electrophoretic velocity of the duplex. A flow is produced in the fluid having a significant component substantially aligned in a direction opposite of the electrophoretic motion of the duplex wherein magnitudes of electric field temperature gradient and flow are such that the duplex will accumulate or be focused at a position along the temperature gradient. A local temperature around the first position is at a first temperature. A focused band of the duplex is detected at the first position thereby determining an amount of the duplex in the focused band at the first temperature. At least one of the electric field, temperature gradient and the flow are progressively changed so that a local temperature around the focused band becomes progressive different than the first temperature. The amount of the duplex is monitored in the focused band. The amount of the duplex is compared in the focused band at each progressively different temperature thereby determining the melting temperature of the duplex.

In accordance with yet another aspect of the present invention, a method is provided for using a temperature gradient focusing device to determine the melting temperature of duplex of a first molecular species and a second molecular species in a fluid. The temperature gradient focusing device has a temperature gradient. The method includes mixing a first molecular species and a second molecular species in a fluid to form a sample solution containing a duplex. The sample solution is introduced into the temperature gradient focusing device. The operational parameters are adjusted in the temperature gradient focusing device so that the duplex is focused at a position along the temperature gradient. A local temperature around the first position is at a first temperature. The focused band of the duplex is detected at the first position thereby determining the amount of the duplex in the focused band at the first temperature. Progressively, the operational parameters are changed so that the local temperature around the focused band becomes progressively different than the first temperature. The amount of the duplex is monitored in the focused band and the amount of the duplex in the focused band is compared at each progressively different temperature thereby determining the melting temperature of the duplex.

One advantage or feature of the present invention is provided by a technique that allows for simultaneous concentration and separation in a manner similar to isoelectric focusing but which is adoptable for use with any charged material and is not limited to materials for a specific isoelectric point or range of isoelectric points. Further, the temperature gradient focusing of the present invention can be used to achieve higher degrees of sample concentration, e.g., more than 10,000 fold concentration of a dilute material, when compared with any prior single sample preconcentration method.

A further feature of the present invention is that the electrophoretic velocity gradient is formed within the channel or capillary in response to the temperature gradient without the need for externally manipulated voltages or complicated and difficult to fabricate semi-permeable structures.

Further features and advantages of the present invention will be set forth in, or apparent from, the detailed description of preferred embodiments thereof which follows.

BRIEF DESCRIPTION OF THE DRAWINGS

The invention will now be described in detail with respect to preferred embodiments with reference to the accompanying drawings, wherein.

plotted as a function of the distance along the microchannel of FIG. 3(a), where $\sigma(T)$ is the temperature dependent conductivity, $\sigma_0$ is a constant, and $\eta(T)$ is the temperature dependent viscosity.

plotted as a function of the distance along the microchannel of FIG. 4(a)

DETAILED DESCRIPTION OF THE INVENTION

Figure 1A:
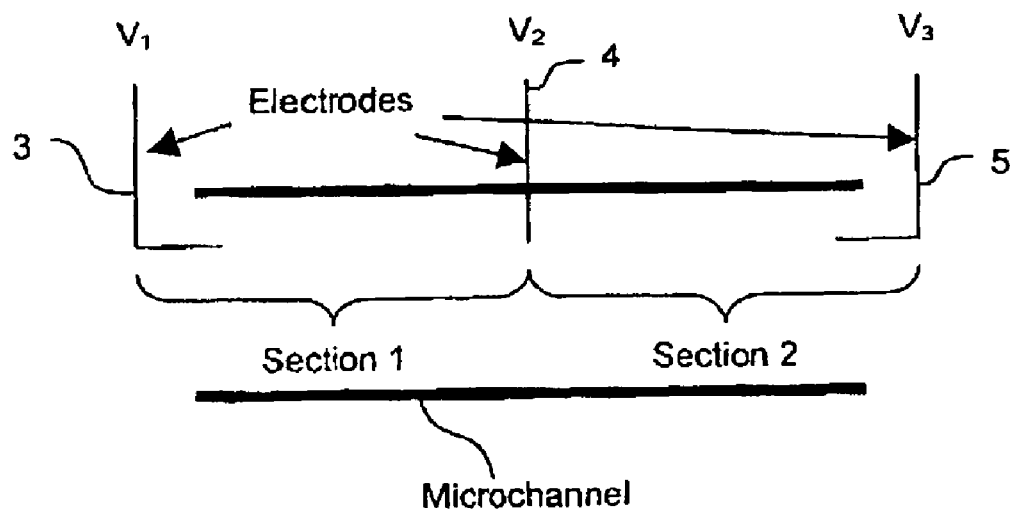
FIG. 1(a) is a schematic depicting a prior art microchannel device which provides for electric field gradient and FIG. 1(b) is a plot of the electric field versus distance (x) along the microchannel of FIG. 1(a)
Figure 1B:
Figure 2:
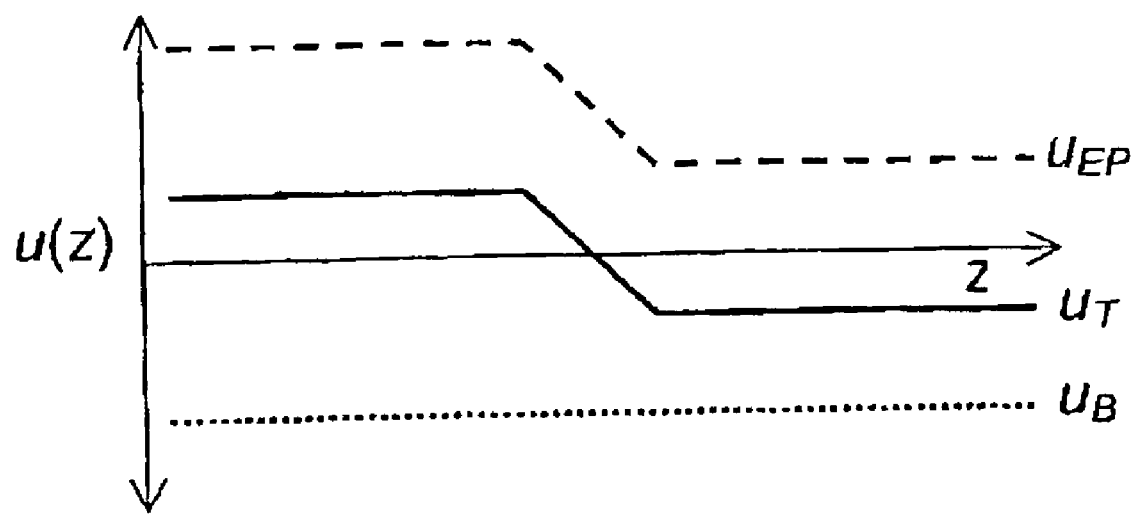
FIG. 2 is a plot of velocity versus distance along the microchannel of FIG. 1(a)

A material can be focused in a fluid conduit such as a channel or capillary when its total velocity is in opposite directions in different portions of the conduit, so that the material will move into the middle of the conduit and stop at a position where its velocity is zero. One way of accomplishing this is to cause the material to move with an electrophoretic velocity that varies along the length of the conduit. This can be accomplished by producing an electrophoretic velocity gradient along the conduit. If an electrophoretic velocity gradient is established, but the electrophoretic velocity is still in the same direction along the entire length of the conduit, a counter-balancing bulk flow can be applied to the fluid in the conduit, driven either by electroosmosis, pressure gradients, or both, so that the total velocity of the material, i.e., the vector sum of the bulk flow velocity and electrophoretic velocity of the material is equal to zero at some position along the conduit.

Temperature gradient focusing is a method for focusing materials that produces the required material electrophoretic velocity gradient through the application of a temperature gradient. In temperature gradient focusing, a fluid with a temperature dependent ionic strength is typically used to give an electrophoretic velocity that is temperature dependent. Then the electrophoretic velocity of the material can be altered in different portions of the conduit or capillary simply by heating or cooling different portions of the conduit. The application of a temperature gradient then results in an electrophoretic velocity gradient, which, with a counteracting bulk flow, can be used for focusing. It should be noted that, in contrast to electric field gradient focusing where the electric field gradient is applied using a combination of electrodes and membranes, using temperature gradient focusing of the present invention, the necessary electric field gradient is produced by the application of a temperature gradient. With temperature gradient focusing, different materials are focused at different positions and thereby separated based upon differences in their electrophoretic mobilities.

In the method of the present invention, temperature gradient focusing is used to first focus one material in a fluid, after which a second material is introduced to the system and allowed to move so that it passes through the focused band of the first material and allowed to interact with it. If the interaction produces a third material, that third material can then also be focused on the temperature gradient (assuming that it is charged and that it has the same sign of charge as the first material). Detection of the focused band of the third material, which is the product of the interaction or reaction of the first two materials, signals that the interaction has occurred. If the product of the interaction is a duplex of the first two materials (or of some parts of the first two materials), further manipulations can then be used to determine the strength of the binding of that duplex by measuring its melting curve and melting temperature.

The types of fluids that would typically be used include ionic aqueous solutions, ionic non-aqueous solutions, aqueous buffer solutions, and mixtures of aqueous and non-aqueous solutions. The types of materials that could be analyzed using this method include any pair of materials in which at least one of the materials is charged when dispersed or dissolved in the fluid used. Specific examples of materials that could be analyzed for their interactions using this method include single stranded DNA, single stranded PNA, single stranded DNA covalently bound to a 'drag tag', nucleic acid aptamers, antibodies, molecules with molecular weight less than 500 amu, amino acids, peptides, proteins, cytokines, nucleic acids, cells, colloidal particles, bacterial particles, and viral particles.

Further description of the present invention will now be made with reference to the drawings, and in particular to FIG. 3(a), where a fluid-filled microchannel 10 includes electrode connections 12, 14 at each end one of which is connected to a high voltage source such as an electrical power supply and the other of which is electrically grounded. The velocity of a material in the microchannel 10 is given by the sum of its electrophoretic velocity, $u_{EP}$, and the bulk velocity, $u_B$, of the fluid:

$$u_T = u_{EP} + u_B.$$

If there is a gradient in the electrophoretic velocity, the bulk velocity can be adjusted so that the total velocity is equal to zero at a single point along the microchannel 10, and the material will be focused at a position around that point. The electrophoretic velocity of a material in the microchannel 10 is given by the product of the electric field, E, and the electrophoretic mobility of the material: $u_{EP} = E \cdot \mu_{EP}$.

Figure 3:
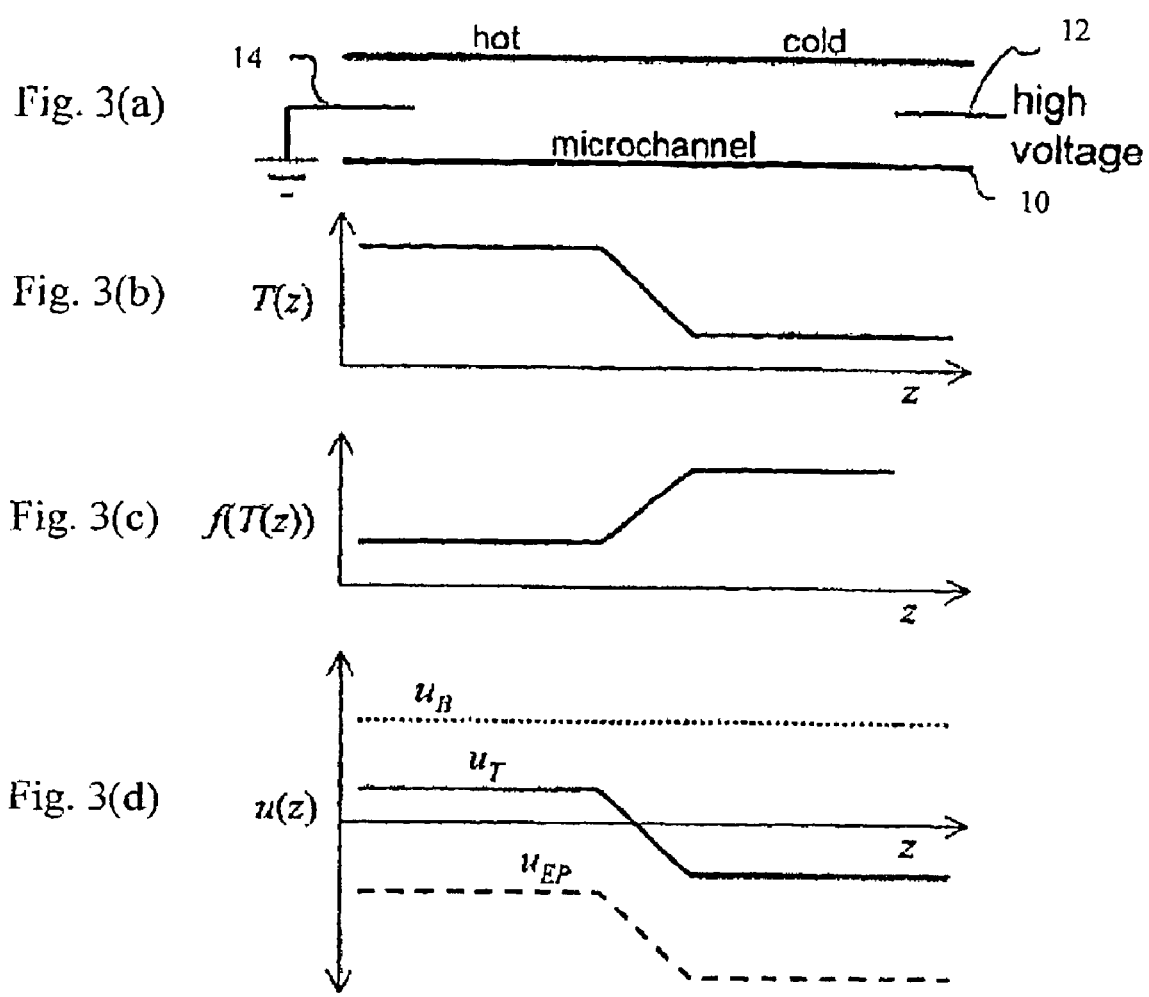
FIG. 3(a) is a schematic illustration of temperature gradient focusing and fluid conduit in the form of a microchannel in accordance with the present invention.
FIG. 3(b) depicts temperature distribution along the microchannel of FIG. 3(a)
FIG. 3(c) is a plot of the function $$f(T) = \frac{\sigma(20) \cdot \eta(20)}{\sigma(T) \cdot \eta(T)}$$
FIG. 3(d) is a plot depicting velocity as a function of distance along the microchannel.

A temperature gradient is applied along the length of the channel as shown in FIG. 3(b). This results in corresponding gradients in both the electric field E and the electrophoretic mobility $\mu_{EP}$.

The electric field in the microchannel 10 is given by:

$$E = \frac{I}{A \cdot \sigma},$$

where I is the electric current running through the microchannel 10, A is the channel cross-sectional area of the microchannel 10, and $\sigma$ is the conductivity of the fluid. Since the conductivity of the fluid is most often temperature-dependent, the electric field is also most often temperature-dependent. Here, constant current is presumed because the current running through any given section of the microchannel 10 will be the same for all parts of the microchannel, whereas the voltage drop across a portion of the microchannel 10 and the electric field in the microchannel 10 will depend on the temperature of that portion. One skilled in the art will readily appreciate that the present temperature gradient focusing differs from electric field gradient focusing in that in electric field gradient focusing, the velocity gradient that is used for focusing results from a gradient in the electric field imposed by the addition or subtraction of current from a point or points within the microchannel.

Using microchannel 10, it is possible to manipulate the conductivity of the fluid by changing the temperature. Consequently, it is possible to produce electric field gradients in microfluidic devices, such as microchannel 10, through the application of a temperature gradient.

At fixed current density, the electric field in microchannel 10 is inversely proportional to the conductivity of the fluid in the microchannel. Most often, the primary temperature dependence of the conductivity is due to the variation of the fluid viscosity with temperature, so it can be written as $\sigma = \sigma_0 \cdot \eta(20)/(\eta(T) \cdot f(T))$, where $\sigma$ is the conductivity, $\sigma_0$ is a constant, $\eta(T)$ is the temperature dependent viscosity, and $f(T)$ is a dimensionless function that accounts for any other temperature dependence. Similarly, the temperature dependence of the electric field is given by $E=E_0 \cdot \eta(T) \cdot f(T)/\eta(20)$, where E is the electric field and $E_0$ is a constant.

For the types of fluids most commonly used microfluidic analysis, e.g., aqueous buffers, the function $f(T)$ is constant or only weakly dependent on temperature. However, it can be non-constant, i.e., variable, if, for example, the ionic strength of the fluid is temperature dependent. Advantageously, the fluids of the present invention are characterized by a non-constant $f(T)$.

The electrophoretic mobility of a material in the fluid is also dependent on the viscosity, and so can be written as $\mu_{EP}=\mu_0 \cdot \eta(20)/(\eta(T) \cdot f_{EP}(T))$, where $\mu_0$ and $f_{EP}(T)$ are defined in analogy to $\sigma_0$ and $f(T)$ where, for most materials, $f_{EP}(T)$ will be constant. The electrophoretic velocity of the material can then be written as $u_{EP}=E_0 \cdot \mu_0 \cdot f(T)/f_{EP}(T)$. It should be noted that if $f(T)$ and $f_{EP}(T)$ have the same temperature dependence, e.g., they are both constant, then $u_{EP}$ will not be temperature dependent, and an electric field gradient produced in this way can not be used for focusing.

If, on the other hand, $f(T)$ and $f_{EP}(T)$ do not have the same temperature dependence, then temperature gradients will result in gradients in the electrophoretic velocity, which can be used for focusing as described above.

One skilled in the art will readily appreciate a major advantage of this present method over some other methods of preconcentration is that the concentrations of the background ions (those ions that are included in the fluid to provide a temperature-dependent ionic strength) are completely unaffected by the focusing. This results from the fact that if the background ions are considered as materials to be focused, then, by definition, $f_{EP}(T)=f(T)$ and there is no gradient in the electrophoretic velocities of the background ions.

Most commonly this technique would be implemented with a fluid characterized by a strongly temperature dependent $f(T)$ and with materials characterized by a constant or nearly constant $f_{EP}(T)$. However, the present temperature gradient focusing can also be implemented in a system in which $f(T)$ is constant and $f_{EP}(T)$ is not, or in which both $f(T)$ and $f_{EP}(T)$ are non-constant, but differ in their temperature dependence. One type of fluid that would have a temperature dependent $f(T)$, and could therefore be used for temperature gradient focusing, would be a fluid with a temperature dependent ionic strength.

One preferred fluid system is composed of 0.9 mol/L Tris (hydroxymethyl)aminomethane and 0.9 mol/L boric acid in water (0.9 M Tris-borate buffer), with an expected pH of about 8.7 (at room temperature). From measurements of the conductivity of the 0.9 M Tris-borate buffer and the known viscosity of water, the function $f(T)$ for 0.9 M Tris-borate buffer was determined to vary from 1 at 20° C. to 0.77 at 70° C.

The counterbalancing bulk flow can be applied electroosmotically if the electro-osmotic mobility does not differ too much from the electrophoretic mobility of the material to be focused. If the electro-osmotic mobility is written as $\mu_{EO}=\mu_{EO}^0 \cdot \eta(20)/\eta(T)$, then by adjusting the ratio of the lengths of the hot and cold channels, (assuming $f_{EP}(T)$=constant) focusing can be achieved if $f(\text{cold})/f(\text{hot})<-\mu_0/\mu_{EO}^0<f(\text{hot})/f(\text{cold})$, where $f(\text{hot})>f(\text{cold})$ (If $f(\text{hot})<f(\text{cold})$, then the inequalities have the opposite sign). If x is the fraction of the total channel length that is hot, then focusing will occur if: $x \cdot f(\text{hot})/f(\text{cold})+(1-x)<-\mu_0/\mu_{EO}^0<+(1-x) \cdot f(\text{cold})/f(\text{hot})$, where $f(\text{hot})<f(\text{cold})$. By adjusting x, it is then possible to tune the range of material mobilities that are focused. In many cases, the electrophoretic and electroosmotic mobilities will not be so well balanced, and therefore although the bulk velocity will be largely due to electroosmosis, it must also be adjusted using an externally applied pressure gradient.

It should be noted that temperature gradient focusing can also be implemented in microchannels or other fluid conduits of non-constant cross-section. The final results are essentially unchanged, since in most instances, the dependence on the cross-sectional area of the channel cancels out in the equations. As a result, it is possible to generate the temperature gradient using Joule heating within the microchannel. This would serve to simplify the design and operation of a microfluidic device using this technique even further, since the focusing and the temperature gradient could be produced using the same voltage source and pair of electrodes as illustrated in FIG. 4(a).

Figure 4:
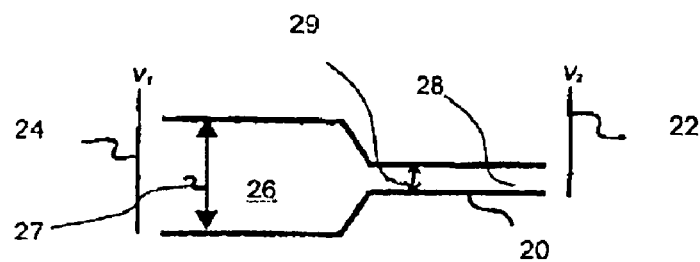
FIG. 4(a) is a schematic illustration of a microchannel for temperature gradient focusing created by Joule heating according to another embodiment of the present invention.
FIG. 4(b) depicts the temperature profile along a length of the microchannel of FIG. 4(a)
FIG. 4(c) is a plot of the function, $$f(T) = \frac{\sigma(20) \cdot \eta(20)}{\sigma(T) \cdot \eta(T)},$$
FIG. 4(d) is a plot showing electrophoretic velocity, bulk velocity, and total velocity vs. distance along the microchannel of FIG. 4(a)
Figure 4:
Figure 4:
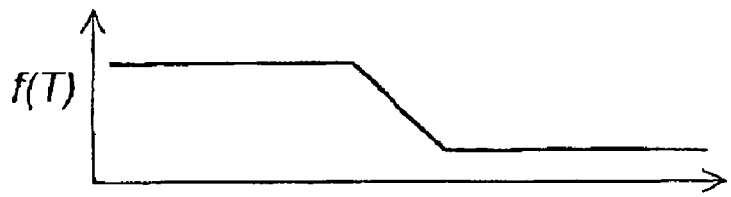
Figure 4:
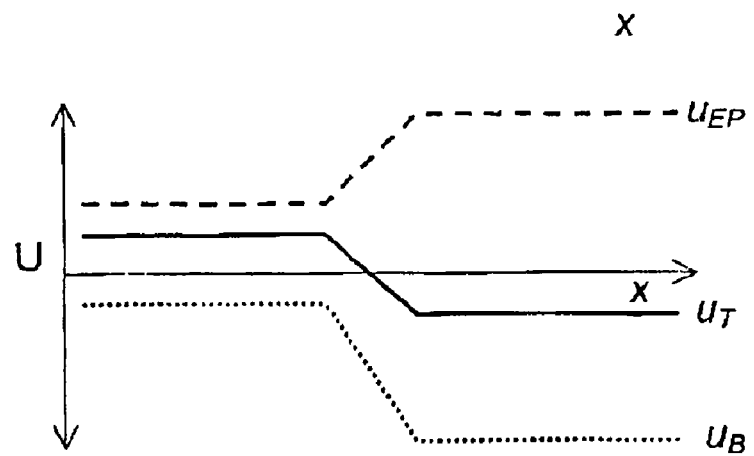

Microchannel 20 shown schematically in FIG. 4(a), has electrodes, 22, 24, and two sections, sections 26, 28, of different cross-sectional area. Section 26 has a cross-sectional area of 27 and section 28 has a cross-sectional area of 29. The electrical resistance per unit length of each section is given by: $R_i=1/(\sigma \cdot A_i)$, where σ is the conductivity of the fluid in the microchannel 20. When a current, I, is passed through the microchannel 20, the power per unit length dissipated through Joule heating in each section will be: $P_i=I^2 \cdot R_i=I^2/(\sigma \cdot A_i)$. In general, the resulting temperature in section 28 will be higher than that in section 26, as shown in FIG. 4(b): $T_2>T_1$. The electric field in each section of the microchannel 20 is given by the current multiplied by the resistance per unit length:

$$E_i=I \cdot R_i=I/(\sigma A_i)=I \cdot \eta(T_i) \cdot f(T_i)/(\sigma_0 \cdot \eta(20) \cdot A_i).$$

The electrophoretic velocity of a material in each section of the channel is: $u_{EP}^i=\mu_0 \cdot f(T_i) \cdot I/(\sigma_0 \cdot f_{EP}(T) \cdot A_i)$. If a bulk flow velocity is applied along the channel, it will not be the same in each section, but will instead be given by $u_B^i=u_B^0/A_i$, where, $u_B^0$ is a constant. The ratio of the electrophoretic velocity to the bulk velocity is then given by: $u_i^{ratio}=\mu_0 \cdot f(T_i) \cdot I/(\sigma_0 \cdot f_{EP}(T) \cdot u_B^0)=u_0^{ratio} \cdot f(T_i)/f_{EP}(T)$ via adjusting $u_B^0$ so that $|u_1^{ratio}|>1>|u_2^{ratio}|$ as shown in FIG. 4(d), which can result in focusing. Because the ratio of the electrophoretic velocity to the bulk velocity does not depend on the cross-sectional areas of the two sections, the same considerations as above apply if bulk flow is applied electroosmotically.

Joule heating may be used to generate the temperature gradient in the microchannel device of FIG. 4(a). The following is a non-limiting example demonstrating Joule heating of a microchannel of the type shown in FIG. 4(a).

The microchannel used for this demonstration was similar to the one shown schematically in FIG. 4(a). The width, i.e., cross sectional area 29, of the narrow channel, i.e., section 28, was about 70 μm, and the width of the wide section, i.e., section 26, cross sectional area 27 was about 350 μm. The length of the tapered portion of the channel was about 500 μm. The depth of all portions of the channel was about 30 μm. The total length of the microchannel was about 2 cm, with the length of the section 28 divided by the total length, x≅0.8. Access to each end of the microchannel was provided by a 3 mm hole through the lid piece of the microchannel.

The fluid used was 0.9 M Tris-borate buffer. The material to be concentrated was the carboxyfluorescein. An 8 μmol/L solution of carboxyfluorescein in the 0.9 M Tris-borate buffer was prepared. Detection of the carboxyfluorescein was performed using a fluorescence microscope and CCD cameras. Simultaneous color and grayscale images were obtained.

To demonstrate gradient focusing using Joule heating, the microchannel was filled with the caboxyfluorescein solution and 1900 V was applied along its length using a high voltage power supply and platinum electrodes, with the positive voltage $V_2$ applied to the narrow end via electrode 22, and the wide end held at ground at electrode 24.

After 6 min., the carboxyfluorescein was highly concentrated at the junction between sections 26 and 28 of the microchannel 20. The concentration factor achieved by using this example was typically about 100-fold per minute.

Figure 5:
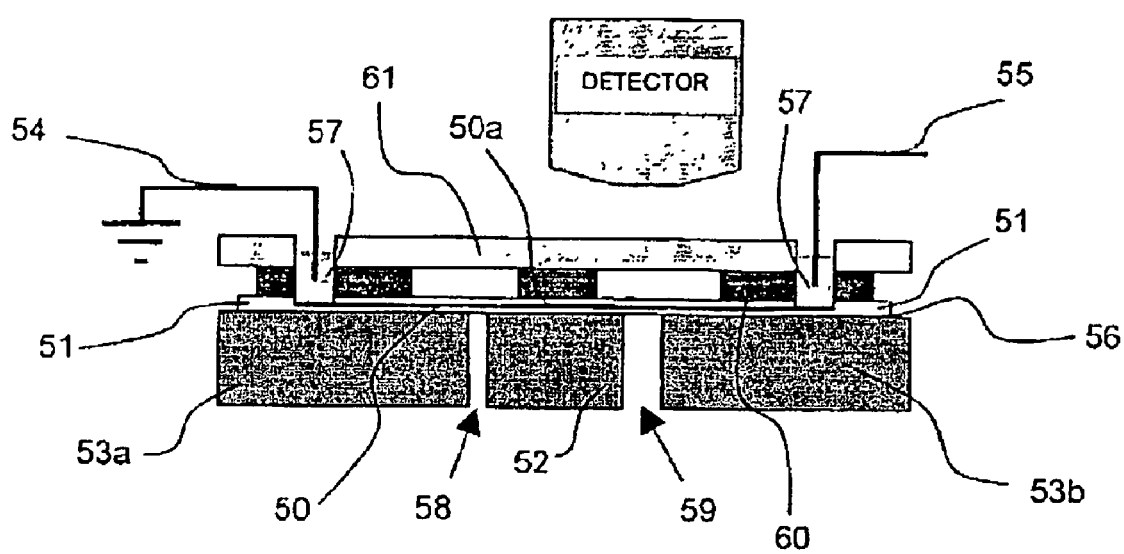
FIG. 5 is a schematic drawing of a fluidic device according to further embodiment of the present invention.

Referring now to FIG. 5, in order to have better control of the temperature gradient, experiments were done using three temperature zones, two cold zones provided by cooling copper blocks 53a, 53b covering much of the ends of the microchannel 50, and one hot zone provided by heated copper block 52. The microchannel 50 was made out of thin (125 μm) sheets of poly(carbonate) substrate 51, which were pressed onto the copper blocks 52, 53a, 53b. Thermal contact between the poly(carbonate) and the copper blocks was insured using a thermally conductive adhesive 56. The copper blocks 52, 53a, 53b were arranged so that there was a 1 mm gap 58 between the heated copper block 52 and the cooling copper block 53a and a 2 mm gap 59 between heated copper block 52 and the cooling copper block 53b.

Microchannel 50 also includes electrodes 55, 54, fluid reservoirs 57, and a narrow hot zone 50a near the middle of the microchannel 50. The heated copper block 52 was heated using a small high-power resistor embedded into the copper and its temperature was regulated using a PID temperature controller (Omega Engineering Inc, Stamford, Conn.). To regulate the temperature of the cold zones, ¼ inch diameter holes were drilled through the cooling copper blocks 53a, 53b and cold water from a thermostatted bath (Neslab, Portsmouth, N.H.) was passed through them.

Thin polycarbonate microchannel chips, i.e. substrate 51 was attached to the copper blocks 52, 53a, 53b using thermally conductive adhesive 56 in the form of transfer tape (3M). The substrate 51 was pressed against the copper blocks 52, 53a, 53b from above with 3 mm thick PDMS (Sylgard 184, Dow Corning, Midland, Mich.) gaskets 60 and a 2 mm thick acrylic (Acrylite OP-4, Cyro Industries, Mt. Arlington, N.J.) top plate 61, which was secured to the outer copper clocks using nylon screws (not shown).

During temperature gradient focusing, a voltage potential is applied to electrode 55 and electrode 54 is set to ground using a high voltage power supply. In most cases, the electrophoretic and electroosmotic mobilities are not sufficiently balanced, so that an externally applied pressure gradient must be applied to microchannel 50 to allow microchannel 50 to provide focusing and separation of different types of materials: small dye molecules, amino acids, proteins, DNA, colloidal particles, and cells. There are many possible means for applying the necessary pressure gradient, including the use of pneumatic pressure controllers, and adjusting the volume of fluid contained in the reservoirs 57 to take advantage of gravitational and/or capillary (surface tension-driven) forces.

The microchannel 50 may be formed by imprinting with a micro machined silicon template and then sealed with a similar material according to the method disclosed in Ross, D.; Gaitan, M.; Locascio, L. E., *Analytical Chemistry* 2001, 73, 4117-23, herein incorporated by reference.

The copper block arrangement was also used to determine the degree of focusing that could ultimately be reached with temperature gradient focusing. Beginning with a 8 nM solution of Oregon Green 488 carboxylic acid in 0.9 M Trisborate, 100 min of focusing resulted in a focused plug of Oregon Green 488 carboxylic acid with a peak concentration over 80 μM—a greater than 10000-fold increase in concentration.

It will become readily apparent to one of ordinary skill in the art that the present method provides for use in numerous applications. For example, temperature gradient focusing could be used as a preconcentration step before an analysis or separation or as a simultaneous concentration and separation technique. In addition, temperature gradient focusing could be used for preparative scale separation of different materials or different enantiomers if the focused material or materials are collected after focusing.

In addition, temperature gradient focusing may be used with any charged material and not just small molecules. For example, the materials may include larger molecules such as proteins and DNA, or even particles and cells. In addition, the present method can be adapted for use to sort particles or cells by electrophoretic mobility.

In one separation mode, the bulk velocity could be ramped over time to scan focused sample peaks past a fixed detector, e.g. the detector shown in FIG. 5. This would produce results similar to capillary electrophoresis but the widths of the sample peaks would be determined by the applied gradients and the peak heights would be determined by how long a given peak was in the focusing "window". If the ramp speed were halved, the peak heights would all be doubled, so that the ramp rate could be chosen dependent on the concentration limit of detection necessary. Alternatively, the focusing window could remain fixed and a scanning or imaging detector could be used to locate the separate peaks.

In a further embodiment, the method may be adapted for a system where temperature dependence is due to something other than the ionic strength. An example is a system having $f(T)$ constant but $f_{EP}(T)$ not constant, or variable. One way to accomplish this would be to use a fluid with a temperature dependent pH. In such a system, this embodiment of the present invention is similar to isoelectric focusing schemes. However, the present invention differs from isoelectric focusing in that, in the present system, an opposing fluid flow is applied so that materials are focused at a pH other than their isoelectric points.

When using any of the embodiments of the present method, operating parameters which include voltage, bulk flow rate, and temperature of the different zones may be held constant with time or varied with time to affect the position and width of focused sample peaks. Varying of parameters may be accomplished using any of a number of methods which include the methods previously described above in which the focused sample peaks are scanned past a fixed detector.

Advantageously, in order to achieve the fastest accumulation of material in the focused peak, the highest possible voltage should be used. However, a higher applied voltage requires a faster bulk flow which can result in greater dispersion, i.e., wider focused peaks, which is disadvantageous for separation and for achieving pre-concentration of a sample to a high concentration in a very narrow peak. Therefore, a high voltage and fast bulk flow could be used for the initial accumulation of material into a relatively broad peak, and the voltage flow and flow rate could then be reduced to the values which give the narrowest peaks. Further, temperature gradients could be turned on and off to first concentrate the sample and then release the focused peak and allow it to flow on down the channel. Further, the temperature gradient can be adjusted to be linear or nonlinear, and the temperature gradient may be monotonic or non-monotonic. Thus, operating parameters may be adjusted to achieve the desired results.

While the previously disclosed embodiments are directed to a microchannel or microfluidic device, the present method may be adapted for incorporation for use with substantially larger channels which may include millimeter and centimeter if not larger in dimension which should now be apparent to one of ordinary skill in the art. Because temperature gradient focusing uses low conductivity fluids, one can adapt the present method for use in much larger scale geometries than the micron-sized channels and capillaries described in detail herein.

Figure 6:
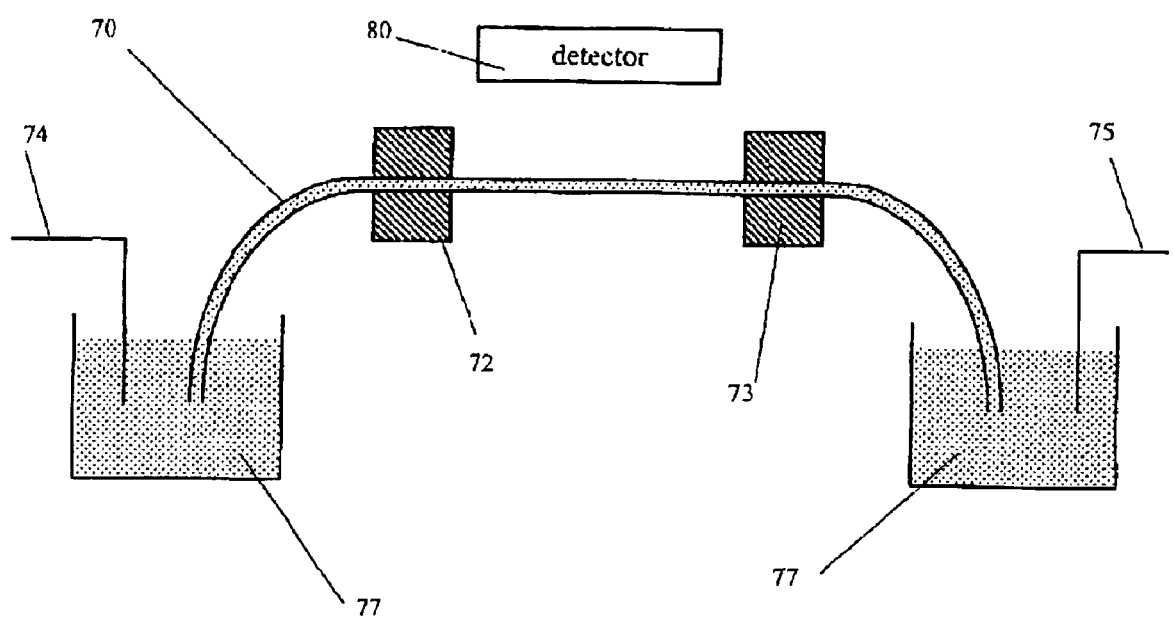
FIG. 6 is a schematic drawing of a capillary fluidic device according to an alternate embodiment of the present invention.

Further, the previously described method can be adapted for use in modified capillary fluidic systems known to one of ordinary skill in the art. FIG. 6 depicts a capillary fluidic system having a capillary tube 70 spanning between two fluid reservoirs 77. Two temperature blocks, denoted as heated block 72 and cooling block 73 are located along the length of the capillary tube 70 to provide a desired temperature gradient in the capillary tube 70. Alternatively, temperature blocks being both cooling, both heated, both at ambient temperature, or any combination, thereof, may be substituted to provide the desired temperature gradient.

The fluid reservoirs 77 contain a fluid with temperature dependent ionic strength. Electrodes 74, 75 are connected at one end to a power supply and on the other end, are in contact with the fluid in the reservoirs 77. The power supply applies a driving voltage through the capillary tube 70. A source of bulk flow is driven either by electro-osmosis with the applied driving voltage, by a pressure gradient applied, e.g. by a pump, or a combination of the two. Detector 80 is used to detect materials present in the fluid.

The temperature gradient focusing technique of the present invention can be used for mixing reactions and for monitoring and/or detecting the interactions between different materials such as interacting molecular species. In one form of mixing reactions/interactions, a material is first focused using temperature gradient focusing as described above with regard to the prior embodiments. Subsequently, a second material is introduced into the fluid conduit and a product of the interaction of the two materials can be focused on the same temperature gradient and detected. The materials and/or their interaction products can be detected in accordance with conventional detection methods known to one of ordinary skill in the art as well as in accordance with previously described detection methods.

Figure 7:
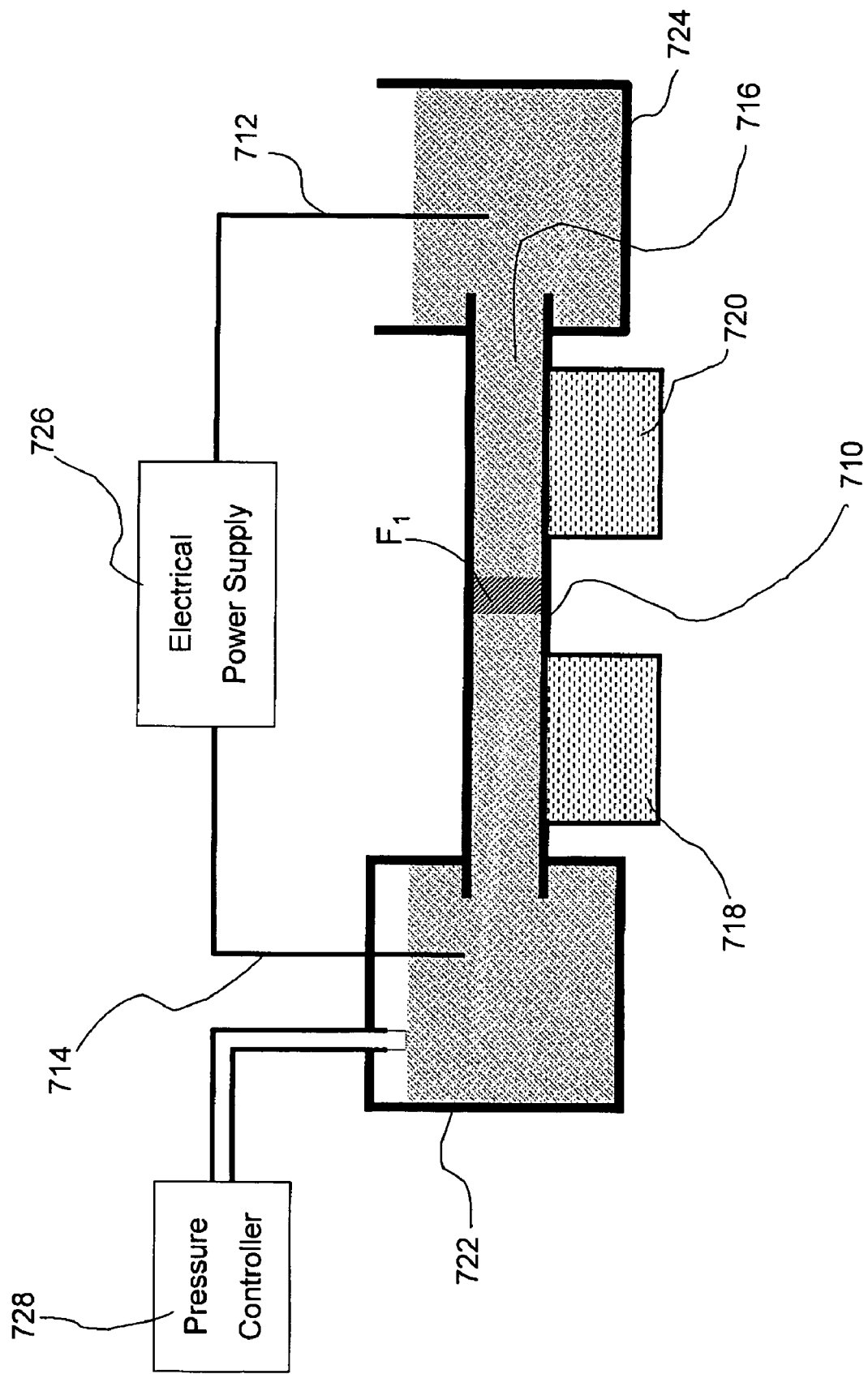
FIG. 7(a) is a schematic drawing depicting a mixing reaction by temperature gradient focusing prior to the addition of the second material.
FIG. 7(b) is a schematic drawing of the mixing reaction of FIG. 7(a) after the addition of second material in accordance with the present invention.
Figure 7:
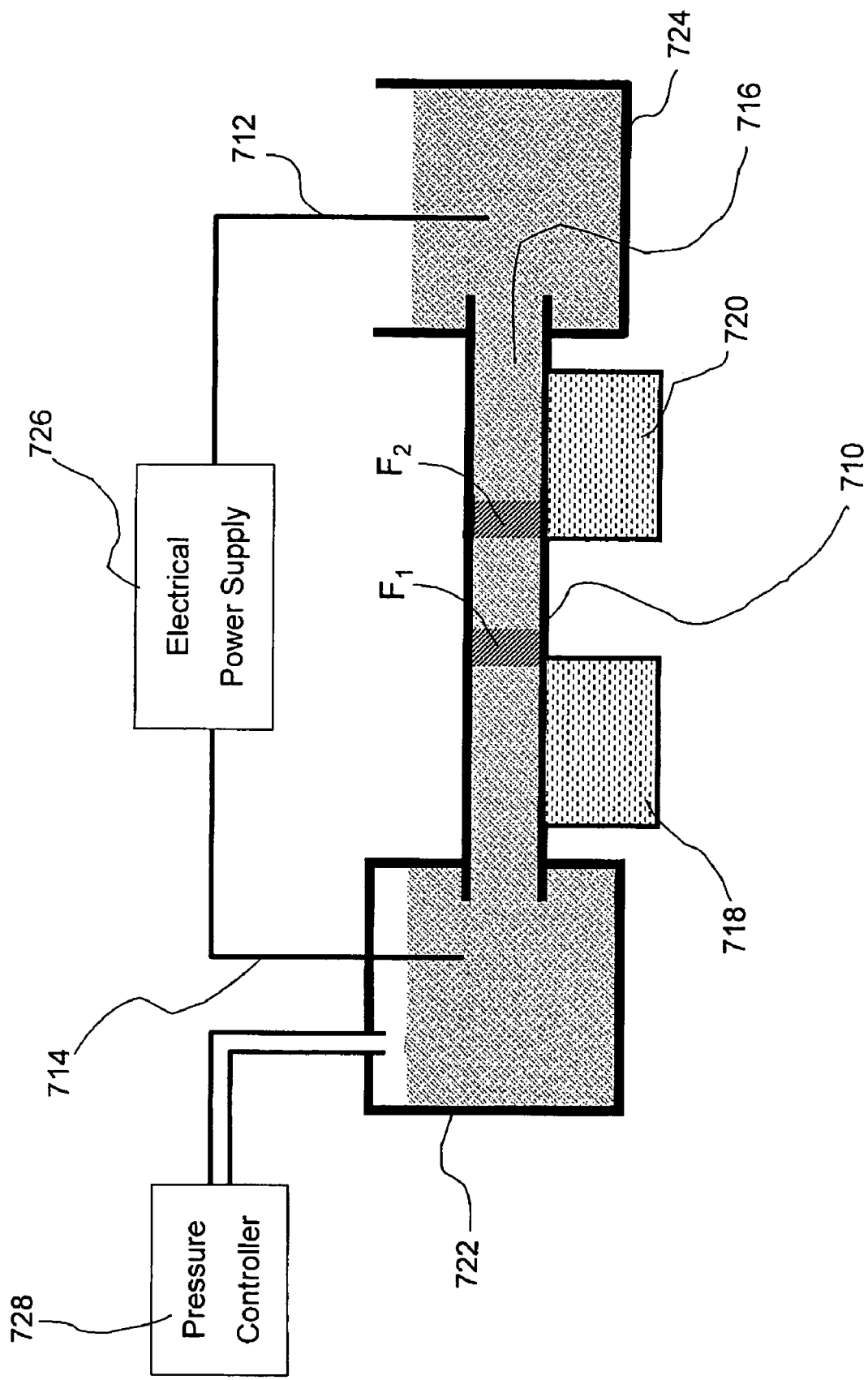

Referring now to FIGS. 7(a) and 7(b), mixing reactions in accordance with the present invention can be conducted using a fluid conduit such as microchannel 710 which comprises a hot zone and a cold zone produced by heated block 718 and cooled block 720, respectively. This creates a temperature gradient in the fluid 716 which contains a first material to be separated or focused. An electric field is established in the fluid 716 by applying a voltage potential to a high voltage electrode 712 so that the voltage between terminal 712 and a grounding electrode 714 causes the first material to move electrophoretically. The voltage is most commonly applied by an electrical power supply 726.

As with the prior embodiments, a temperature gradient is established along the length of the microchannel 710 which has a significant component substantially aligned with the electric field to thereby generate a gradient of the electrophoretic velocity of the first material. The gradient of electrophoretic velocity of the first material can be established by the fluid 716 having an ionic strength or pH which is temperature dependent as described above.

A bulk flow is produced in the fluid 716 due to electroosmosis resulting from the applied voltage and adjusted via pressure controller 728 to have a significant component substantially aligned in the direction opposite of the direction of the electrophoretic migration of the first material so that the total velocity of the first material is equal to zero at a position along the microchannel and a focused band of material $F_1$ will form at that position. The bulk flow is established in a similar manner to that described with regard to the prior embodiments.

Next, a second material is introduced into the fluid so as to move through the now focused first material band $F_1$, and to interact with the first material. The second material can be introduced to either end of the microchannel, depending on whether it has an electrophoretic mobility that is less than or greater than that of the first material. If the electrophoretic mobility of the second material is less than that of the first material, or if the second material is of the opposite charge than the first material, then the second material should be introduced into the end of the channel where the bulk fluid flow predominantly determines the direction of motion of the first material. More specifically, if a fluid with a temperature-dependent ionic strength is used, the second material should be introduced into the high ionic strength end. If, on the other hand, the second material has an electrophoretic mobility that is greater than that of the first material, assuming that they have the same sign of charge, it should be introduced into the end of the channel where the electrophoretic motion dominates or the low ionic strength end.

After the second material is introduced, if hybridization, binding, or other interaction or chemical reaction of the two materials occurs, the product of that interaction, i.e., a third material, will be focused at a second position and a second band $F_2$ will be observed as depicted in FIG. 7(b).

Preferably, the position of the second band $F_2$ will be different than the position of the first band $F_1$, due to a difference in electrophoretic mobility.

In a non-limiting example of this method, this method can be used to observe the interaction of single strand DNA with another nucleic acid. In this example, the first material is negatively charged single stranded (ss) DNA which is labeled for observation within the microchannel 710, and the second material is a peptide nucleic acid (PNA) which is introduced into the microchannel 710. First, the ssDNA is focused as a single band F1. Then, the neutral PNA is introduced into the microchannel 710. The PNA is carried by the bulk flow of the fluid through the stationary, focused band of single strand DNA at location F1.

The ssDNA and PNA are allowed to interact with each other. If the PNA and ssDNA hybridize, the hybrid duplex will focus at a different spatial location within microchannel 710 because of its different electrophoretic mobility and as a result a second band, $F_2$, is observed. If the PNA is not complimentary to the focused ssDNA, the two will not hybridize with one another and the neutral PNA will remain unfocused. In such an instance, a second band will not be observed and the result will be the same as shown in FIG. 7(a).

Figure 8:
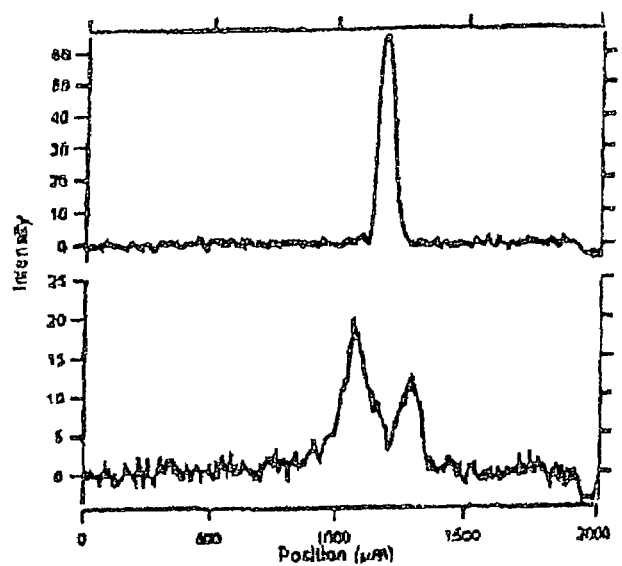
FIG. 8 is a plot relating intensity versus distance along a temperature gradient prior to the addition of the second material (top panel) and after the addition of the second material (bottom panel)

The following non-limiting example is included to provide further understanding of the present mixing reaction method using temperature gradient focusing. The ssDNA was fluorescently labeled on the 5' end while the PNA probes contained a fluorescence label on the N-Terminus. The labels were fluorescein for DNA (green emission) and TAMRA for PNA (orange emission). Using a VHS tape and frame grabbing software, the hybridization of a perfect complement PNA probe to ssDNA was recorded. The experiment was performed in a 30 µm I.D. fused silica capillary, 10 cm long. The capillary was mechanically and thermally anchored to two copper blocks at different temperatures to create a temperature gradient along a 2 mm section approximately midway along the length of the capillary. A temperature gradient from 10° C. to 80° C. was applied. The fluid used was 0.1 mol/L Tris(hydroxymethyl)aminomethane, 0.1 mol/L phenol in water (0.1 M Tris-phenol buffer). A voltage of +3000 V was applied to the 10° C. end of the capillary and the 80° C. end was electrically grounded. FIG. 8 is the line profile monitoring the fluorescence emission from the PNA/DNA duplex that resulted from the mixing and the unreacted ssDNA. In FIG. 8, the top panel is a plot depicting a line profile before the introduction of PNA into the bulk flow and the bottom panel is a plot depicting a line profile 20 minutes after the introduction of PNA into the bulk flow. The single peak in the top panel is the ssDNA after 10 minutes of focusing from an initial concentration of 0.4 μm. The bottom panel shows two peaks corresponding to the PNA/DNA duplex and free ssDNA.

Additional experiments were performed with different ssDNA sequences that included perfect matches and perfect mismatches to a PNA probe sequence. The mismatched sequences did not hybridize and a new fluorescent band was not observed.

In an alternative measurement using temperature gradient focusing, the interactions between two materials are observable as a function of spatial position within a temperature gradient. For example, this method can be used to study duplex matching by first mixing together the two materials and allowing the two to hybridize to form a duplex. Subsequently, the hybridized sample is then focused along the cold side of the microchannel 710. The bulk flow is then adjusted so that the duplex moves towards the hot side of the fluid conduit. The duplex can be detected along the temperature gradient and the melting temperature of the duplex can be measured by detecting the change in intensity of the duplex peak as it is moved towards the hot end of the gradient. When the duplex reaches a position along the gradient where the local temperature is equal to the melting temperature of the duplex, the two materials forming the duplex will come apart and move away from the focused duplex band, and the duplex band will consequently decrease in intensity.

Figure 9:
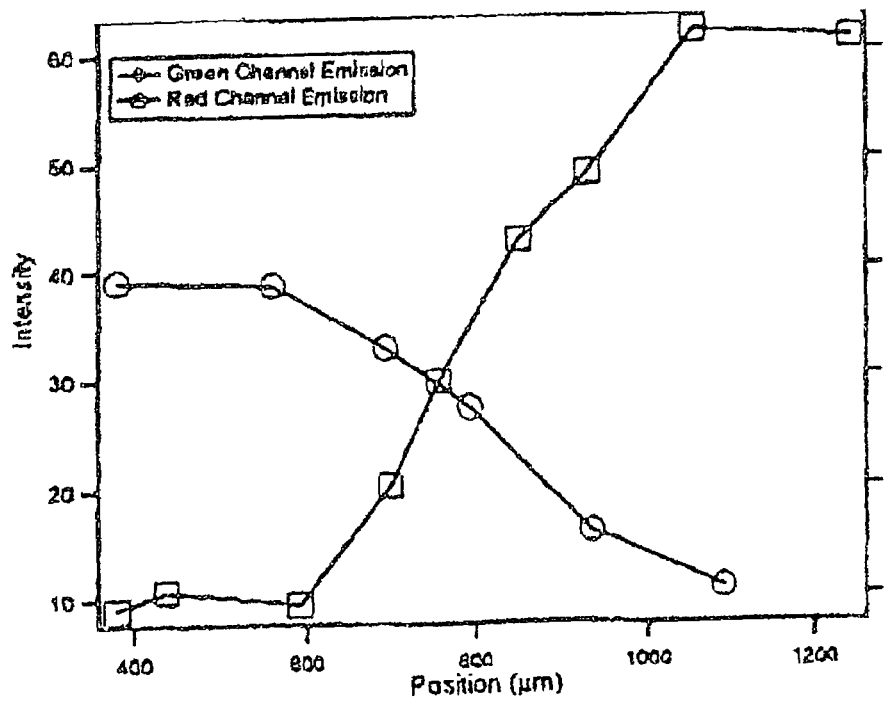
FIG. 9 is a plot depicting fluorescence intensity plotted as a function of position along a separation conduit in accordance with one embodiment of the temperature gradient focusing method of the present invention.

The following non-limiting example is provided to give a better understanding of how the interaction between two materials can be observed using temperature gradient focusing. In this example, a fluorescence melting profile of a PNA/DNA duplex that contained a single base pair mismatch (SBPM) was studied. The temperature gradient focusing separation was performed in a 30 μm I.D. fused silica capillary, 3 cm long. The capillary was mechanically and thermally anchored to two copper blocks at different temperatures to create a temperature gradient along a 2 mm section approximately midway along the length of the capillary. A temperature gradient from 20° C. to 80° C. was applied. The fluid used was 0.1 mol/L Tris(hydroxymethyl)aminomethane, 0.1 mol/L phenol in water (0.1 M Tris-phenol buffer). A solution of equal amounts of the PNA and DNA was prepared in the 0.1 M Tris-phenol buffer and introduced into the capillary via a fluid reservoir on the 20° C. end of the capillary. A voltage of +2000 V was applied to the 20° C. end of the capillary and the 80° C. end was electrically grounded. The pressure applied to the 80° C. end of the capillary was adjusted to control the bulk flow rate so that the PNA/DNA duplex was first focused on the 20° C. end of the 2 mm gradient section. The bulk flow was then progressively adjusted so that focused duplex band was moved spatially from the 20° C. end to the 80° C. end of the 2 mm gradient section. A plot of the measured fluorescence intensity as a function of distance along the gradient section is shown in FIG. 9 with the 20° C. on the right side of the graph and the 80° C. end on the left side of the graph. The green channel emission (circles) corresponds to free ssDNA while the red channel emission (squares) corresponds to the PNA/DNA duplex that contains a single base pair mismatch. The melting temperature can be identified as the temperature at the position where the red channel curve has decreased to about half its initial intensity (approximately 800 μm in FIG. 9). Additional experiments compared the results obtained with a single base pair mismatch with those obtained when the DNA and PNA sequences were perfectly matched. After measuring the temperature inside the capillary to determine the temperature at each position along the capillary, a 7° C. difference was observed in the melting temperature between the perfect match and the single base pair mismatch. This result is comparable to results obtained with conventional UV absorbance-based melting curve experiments.

The two examples described above can be combined in an assay to first determine if there is a hybridization or binding interaction between two materials, and then if a hybridization event occurs, further testing of the melting temperature of the duplex can be performed by scanning the focused duplex through the temperature gradient and monitoring the signal as a function of position. The assay involves focusing ssDNA on the cold side of the gradient, and then flowing the PNA through the sample. If a hybridization event occurs, the resulting focused duplex peak can be concentrated on the cold side of the gradient to a desired concentration before sequentially scanning through the temperature gradient by changing the bulk flow so the duplex will move from cold to hot side of the gradient. The melting temperature can be determined from data such as the melting curve shown in FIG. 9. Comparisons of different melting curves and melting temperatures can then be used to determine the degree of mismatch (perfect match, single base pair mismatch, etc.) of the DNA and PNA sequences.

In another form of a mixing reaction/interaction using temperature gradient focusing, the PNA material can be replace with a second single stranded DNA material that has been covalently or otherwise bound to a 'drag tag' or a molecule with an electrophoretic mobility that is less than that of the single stranded DNA by modifying the teaching of Vreeland, W. N., Meagher, R. J. & Barron, A. E. (2002) *Analytical Chemistry* 74, 4328-4333. Normally, there is only a very small difference in the electrophoretic mobility of single stranded and double stranded DNA. Consequently, it would be difficult to resolve the focused bands corresponding to the free single stranded DNA and the DNA/DNA duplex. Drag tags would therefore be used to reduce the electrophoretic mobility of the second single stranded DNA so that the drag-tag-DNA/DNA duplex would focus at a different position than the first single stranded DNA, so that both could be independently detected.

The present mixing reactions/interactions temperature gradient focusing can also be used to study enzyme/substrate interactions. For example, an enzyme could be initially focused within the separation conduit. The substrate could then be added to the bulk flow. The appearance of a focused product would signify that the enzyme/substrate reaction had occurred. Alternatively, the substrate could be focused first and subsequently introduce the enzyme into the bulk flow.

The present temperature gradient focusing methods for mixing reactions/interactions can be combined by selecting various aspects of the previously described methods. For example, nucleic acid-protein interactions or those that involve drug-target binding events can be analyzed using the present method. The only requirement is that at least one of the two input materials can be focused using temperature gradient focusing.

It will now be apparent to one of ordinary skill in the art that the present mixing reaction using temperature gradient focusing provides the ability to the concentrate targets prior to the assay reaction, with no theoretical limit to the concentration factor. This leads to assays with improved detection limits. This is in contrast to prior methods of concentrating a target which is difficult in affinity based capillary electrophoresis assays and typically involves a pre-concentration step.

Another advantage of the present method is the ability to mix constituents within a microfluidic geometry that does not require complex channel geometries or channel modifications. Because of the low Reynold's number in microfluidic devices, mixing two fluid streams together by diffusion alone can require unacceptably long channel lengths. One way to overcome this is to introduce geometries that facilitate mixing such as serpentine channels or slanted wells ablated into channels. With temperature gradient focusing, the focusing mechanism isolates one of the species to be mixed in a unique spatial location while the second species is allowed to flow through the focused band by bulk flow (or by a combination of bulk flow and electrophoretic motion if the second species is charged). This allows for mixing to occur over small length scales, e.g. 50-200 μm defined by the length of the focused band. In addition, the labeling for detection, e.g. target or probe is simplified because only one needs to be labeled since the product of the target and probe focuses in a unique location.

A further advantage of processing PNA/DNA duplexes through a temperature gradient, e.g., determining melting temperatures of duplexes, is that the present method requires much lower concentration samples. A conventional UV absorbance-based melting temperature measurement typically requires μM levels of DNA samples while temperature gradient focusing only requires nM to pM levels, an improvement of 3-6 orders of magnitude.

In addition, the present temperature gradient focusing-based analysis can also be performed faster than the conventional UV absorbance-based melting temperature measurement, e.g., 5 min compared to 60 min as initially demonstrated. In addition to melting curves of PNA/DNA duplexes, the scanning temperature gradient focusing can be used for any temperature dependent assay, e.g. polymer precipitation reactions.

One of ordinary skill in the art now will readily appreciate that the present temperature gradient focusing differs from prior art methods such as sample stacking and isotachophoresis. In both cases, samples are focused or concentrated as a result of gradients in their electrophoretic velocities. In sample stacking and isotachophoresis, the velocity gradients are generated at the interfaces between solutions of different composition, and the position at which the concentration or focusing occurs is not stationary, but moves along with the electroosmotic flow in the channel or capillary. In contrast to both sample stacking and isotachophoresis, the velocity gradients that produce material focusing in the present temperature gradient focusing result from applied temperature gradients.

Further, one skilled in the art will recognized that the present temperature gradient focusing differs from isoelectric focusing techniques such as those disclosed in U.S. Pat. Nos. 3,664,939 and 5,759,370. Unlike isoelectric focusing techniques in which the pH gradient is established by using a fluid system that has a temperature dependent pH, the present temperature gradient focusing typically utilizes a fluid that has a temperature dependent ionic strength. When a temperature gradient and a voltage are applied to a microchannel, the ionic strength gradient of the fluid gives rise to a velocity gradient, which is used for focusing. As a result, a material present in the fluid is focused at a position where the material's total velocity, i.e., the sum of the electrophoretic velocity of the material and the bulk velocity of the fluid is zero. Therefore, in the present temperature gradient focusing, the pH and the isoelectric point of the material are typically not critical. In the embodiment of the present invention that utilizes fluids with a temperature-dependent pH, and thereby uses a thermally generated pH gradient for focusing, a bulk fluid flow is applied so that rather than focusing at its isoelectric point as in isoelectric focusing, a material will focus at a position along the pH gradient where the local pH is unequal to the isoelectric point of the material.

It will now be apparent to one of ordinary skill in the art that the present temperature gradient focusing method provides numerous advantages over prior methods. The present method is simpler to implement as no imbedded electrodes or salt bridges are necessary. In addition, like isoelectric focusing, temperature gradient focusing can be used to both concentrate and separate materials, but without the disadvantages associated with isoelectric focusing.

A further advantage of the present invention is provided in that only a single, continuous fluid system is required. Solid phase extraction and related preconcentration methods of the prior art require multiple fluids where one fluid is used to carry the material to the preconcentrator and a second fluid is used to release the material from the preconcentrator. Further examples of multiple fluid systems include sample stacking, field amplified injection, isotachophoresis, and sweeping.

Further, the present temperature gradient focusing provides enhanced concentration when compared with the prior art of other single preconcentration methods.

Although the invention has been described above in relation to preferred embodiments thereof, it will be understood by those skilled in the art that variations and modifications can be effected in these preferred embodiments without departing from the scope and spirit of the invention.

What is claimed is:

1. A method for analyzing the interaction between a first material and a second material in a fluid, said interaction giving rise to a third material, said method comprising the steps of:

introducing a first material to a fluid;

applying an electric field to said fluid thereby causing said first material to move electrophoretically with an electrophoretic velocity;

establishing a temperature gradient in said fluid having a significant component substantially aligned with the electrophoretic motion of said first material, thereby generating a gradient of the electrophoretic velocity of said first material;

producing a flow of said fluid having a significant component substantially aligned in a direction opposite a direction of the electrophoretic motion of said first material;

wherein magnitudes of said electric field, said temperature gradient, and said flow are such that said first material will accumulate or be focused at a first position along said temperature gradient; and introducing a second material to said fluid so that said second material moves through said first position, thereby interacting with said first material to form a third material;

whereby said third material of said interaction is then focused at a second position along said temperature gradient.

2. The method of claim 1, wherein an ionic strength of said fluid is temperature dependent and said temperature gradient establishes a gradient in the ionic strength of said fluid.

3. The method of claim 2, wherein:
said first material is a first single stranded DNA molecule and said second material is selected from the group consisting of a second single stranded DNA molecule, a single stranded PNA molecule, and a third single stranded DNA molecule covalently bound to a molecular species having an electrophoretic mobility substantially different from the electrophoretic mobility of said first single stranded DNA molecule; and
said third material is a duplex of said first material and said second material.

4. The method of claim 2, wherein said first material is selected from the group consisting of nucleic acid aptamers and antibodies, and said second material is selected from the group consisting of amino acids, peptides, proteins, cytokines, nucleic acids, cells, colloidal particles, bacterial particles, and viral particles.

5. The method of claim 2, wherein said first material is selected from the group consisting of amino acids, peptides, proteins, cytokines, nucleic acids, cells, colloidal particles, bacterial particles, and viral particles, and said second material is selected from the group consisting of nucleic acid aptamers and antibodies.

6. The method of claim 2, wherein said first material is a substrate, said second material is an enzyme, and said third material is the product of a reaction between said enzyme and said substrate.

7. The method of claim 2, wherein said first material is an enzyme, said second material is a substrate, and said third material is the product of a reaction between said enzyme and said substrate.

8. The method of claim 2, wherein said first material and said second material together produce a chemical reaction to form said third material.

9. The method of claim 2, wherein said first material is a drug and said second material is a target molecular species, and said third material is a complex of said drug and said target molecular species.

10. The method of claim 2, wherein said first material is a first protein and said second material is a second protein and said third material is a complex of said first protein and said second protein.

11. The method of claim 2, wherein said first material and said second material are both fluorescently labeled for detection along the temperature gradient.

12. The method of claim 2, wherein said fluid is selected from the group consisting of ionic aqueous solutions, ionic non-aqueous solutions, aqueous buffer solutions, and mixtures of aqueous and non-aqueous solutions.

13. The method of claim 2, wherein said electric field is applied using a set of components comprising an electrical power supply and two or more electrodes contacting said fluid.

14. The method of claim 2, wherein said step of establishing a temperature gradient comprises applying an electric current to said fluid to produce said temperature gradient by Joule heating.

15. The method of claim 2, wherein said step of establishing a temperature gradient comprises supplying thermal energy to said fluid via a heated block.

16. The method of claim 2, wherein said step of establishing a temperature gradient comprises removing thermal energy from said fluid via a cooled block.

17. The method of claim 2, wherein said flow is generated by electroosmosis.

18. The method of claim 2, wherein said flow is generated by pressure gradients.

19. The method of claim 2, wherein said flow is generated by a combination of electroosmosis and pressure gradients.

20. The method of claim 2, wherein said step of applying an electric field, said step of establishing a temperature gradient, and said step of producing a bulk flow are comprised of using an electrical power supply to apply a voltage to said fluid, and wherein the electric field provided by said electrical power supply causes the electrophoretic motion of said first material, a flow of electric current in said fluid thereby generating said temperature gradient by Joule heating, and electroosmosis of said fluid thereby producing said flow of said fluid.

21. The method of claim 2, wherein said step of applying an electric field and said step of producing a bulk flow comprise using an electrical power supply to apply a voltage to said fluid, and wherein the electric field provided by said electrical power supply causes the electrophoretic motion of said first material, and electroosmosis of said fluid thereby producing said flow of said fluid.

22. The method of claim 2, wherein said third material is a duplex of said first material and said second material, and the magnitude of said flow is initially adjusted so that a local temperature at said second position is a first temperature; and further comprising the steps of:
detecting a focused band of said duplex at said second position, thereby determining an amount of said duplex in said focused band at said first temperature;
changing at least one of the group consisting of said electric field, said temperature gradient, and said flow so that a local temperature around said focused band of said duplex is at a second temperature;
detecting the focused band of said duplex at said second temperature, thereby determining an amount of said duplex in said focused band at said second temperature; and
comparing the amount of said duplex in said focused band at said first temperature to the amount of said duplex in said focused band at said second temperature,
thereby determining if said interaction is different at said first temperature and said second temperature.

23. The method of claim 2, wherein said third material is a duplex of said first material and said second material, said duplex having a characteristic melting temperature, and the magnitude of said flow is initially adjusted so that a local temperature at said second position is a first temperature; and further comprising the steps of:
detecting a focused band of said duplex at said second position, thereby determining an amount of said duplex in said focused band at said first temperature;
progressively changing at least one of the group consisting of said electric field, said temperature gradient, and said flow so that the local temperature around said focused band becomes progressively different than said first temperature;
monitoring the amount of said duplex in said focused band; and
comparing the amount of said duplex in said focused band at each progressively different temperature,
thereby determining the melting temperature.

24. The method of claim 2, wherein said first material is selected from the group consisting of single stranded DNA, single stranded PNA, single stranded DNA covalently bound to a molecular species having an electrophoretic mobility substantially different from the electrophoretic mobility of single stranded DNA, nucleic acid aptamers, antibodies, molecules with molecular weight less than 500 amu, amino acids, peptides, proteins, cytokines, nucleic acids, lectins, and carbohydrates; and said second material is selected from the group consisting of single stranded DNA, single stranded PNA, single stranded DNA covalently bound to a molecular species having an electrophoretic mobility substantially different from the electrophoretic mobility of single stranded DNA, nucleic acid aptamers, antibodies, molecules with molecular weight less than 500 amu, amino acids, peptides, proteins, cytokines, nucleic acids, lectins, and carbohydrates.

25. A method for determining the melting temperature of a duplex of a first molecular species and a second molecular species in a fluid, said method comprising the steps of:

mixing a first molecular species and a second molecular species in a fluid to form a sample solution containing a duplex;

applying an electric field to said fluid thereby causing said duplex to move electrophoretically with an electrophoretic velocity;

establishing a temperature gradient in said fluid having a significant component substantially aligned with the electrophoretic motion of said duplex, thereby generating a gradient of the electrophoretic velocity of said duplex;

producing a flow of said fluid having a significant component substantially aligned in a direction opposite a direction of said electrophoretic motion of said duplex;

wherein magnitudes of said electric field, said temperature gradient, and said flow are such that said duplex will accumulate or be focused at a first position along said temperature gradient, a local temperature around said first position being at a first temperature;

detecting a focused band of said duplex at said first position, thereby determining an amount of said duplex in said focused band at said first temperature;

progressively changing at least one of the group consisting of said electric field, said temperature gradient, and said flow, so that a local temperature around said focused band becomes progressively different than said first temperature;

monitoring the amount of said duplex in said focused band; and comparing the amount of said duplex in said focused band at each progressively different temperature, thereby determining the melting temperature of the duplex.

26. The method of claim 25, wherein an ionic strength of said fluid is temperature dependent and said temperature gradient establishes a gradient in the ionic strength of said fluid.

27. The method of claim 26, wherein said first molecular species is selected from the group consisting of single stranded DNA, single stranded PNA, single stranded DNA covalently bound to a molecular species having an electrophoretic mobility substantially different from the electrophoretic mobility of single stranded DNA, nucleic acid aptamers, antibodies, molecules with molecular weight less than 500 amu, amino acids, peptides, proteins, cytokines, nucleic acids, lectins, and carbohydrates; and said second molecular species is selected from the group consisting of single stranded DNA, single stranded PNA, single stranded DNA covalently bound to a molecular species having an electrophoretic mobility substantially different from the electrophoretic mobility of single stranded DNA, nucleic acid aptamers, antibodies, molecules with molecular weight less than 500 amu, amino acids, peptides, proteins, cytokines, nucleic acids, lectins, and carbohydrates.

28. A method for using a temperature gradient focusing device to determine the melting temperature of a duplex of a first molecular species and a second molecular species in a fluid, said temperature gradient focusing device having a temperature gradient, said method comprising the steps of:

mixing a first molecular species and a second molecular species in a fluid to form a sample solution containing a duplex;

introducing said sample solution into said temperature gradient focusing device;

adjusting operational parameters of said temperature gradient focusing device so that said duplex is focused at a first position along said temperature gradient, a local temperature around said first position being at a first temperature;

detecting the focused band of said duplex at said first position, thereby determining the amount of said duplex in said focused band at said first temperature;

progressively changing said operational parameters so that the local temperature around said focused band becomes progressively different than said first temperature;

monitoring the amount of said duplex in said focused band; and comparing the amount of said duplex in said focused band at each progressively different temperature, thereby determining the melting temperature of the duplex.

29. The method of claim 28, wherein said first molecular species is selected from the group consisting of single stranded DNA, single stranded PNA, single stranded DNA covalently bound to a molecular species having an electrophoretic mobility substantially different from the electrophoretic mobility of single stranded DNA, nucleic acid aptamers, antibodies, molecules with molecular weight less than 500 amu, amino acids, peptides, proteins, cytokines, and nucleic acids; and said second molecular species is selected from the group consisting of single stranded DNA, single stranded PNA, single stranded DNA covalently bound to a molecular species having an electrophoretic mobility substantially different from the electrophoretic mobility of single stranded DNA, nucleic acid aptamers, antibodies, molecules with molecular weight less than 500 amu, amino acids, peptides, proteins, cytokines, and nucleic acids.

* * * * *